United States Patent [19]

Wepplo et al.

[11] 4,252,814

[45] Feb. 24, 1981

[54] OVICIDAL AND LARVICIDAL CYANOMETHYL THIOESTERS

[75] Inventors: Peter J. Wepplo, Princeton; Donald P. Wright, Jr., Hopewell Township, Mercer County, both of N.J.

[73] Assignee: American Cyanamid Company, Stamford, Conn.

[21] Appl. No.: 54,740

[22] Filed: Jul. 5, 1979

[51] Int. Cl.$^3$ .................. A01N 37/34; A01N 43/40; C07C 153/07; C07D 213/83

[52] U.S. Cl. .................. 424/266; 260/347.2; 260/455 R; 424/263; 424/285; 424/301; 546/226; 546/230; 546/313; 546/315

[58] Field of Search ............ 260/455 R, 347.2; 424/301, 263, 266, 285; 546/3 B, 314, 315, 313

[56] References Cited

U.S. PATENT DOCUMENTS

| | | | |
|---|---|---|---|
| 2,307,679 | 1/1943 | Hechenbleikner | 260/455 B X |
| 2,630,448 | 3/1953 | Crouch et al. | 260/455 R |
| 3,226,416 | 12/1965 | Bikales | 260/455 B |
| 3,646,094 | 2/1972 | Brooks et al. | 260/455 B |
| 3,666,738 | 5/1972 | Burke et al. | 260/455 B X |
| 3,867,543 | 2/1975 | Kohn | 424/301 |

OTHER PUBLICATIONS

Ohta et al., Chemical Abstracts, vol. 60, 5472–5473 (1964).
Previero et al., Chemical Abstracts, vol. 73, 77602n (1970).
Dinizo et al., J. Org. Chem., vol. 41, No. 17, pp. 2846–2849, (1976).

*Primary Examiner*—Dolph H. Torrence
*Attorney, Agent, or Firm*—H. G. Jackson

[57] ABSTRACT

There are provided novel cyanomethyl thioester compounds useful as ovicidal and larvicidal agents effective for the control of insects.

22 Claims, No Drawings

OVICIDAL AND LARVICIDAL CYANOMETHYL THIOESTERS

The invention relates to novel cyanomethyl thioesters represented by the formula:

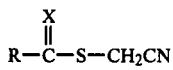
   (I)

wherein X is oxygen or sulfur; R is selected from alkyl $C_2$-$C_4$,

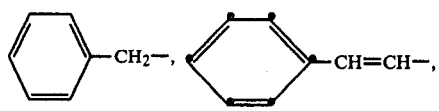

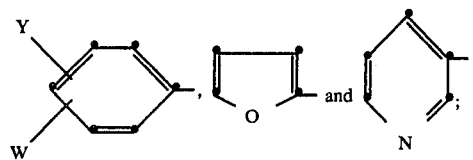

Y is selected from halogen, alkyl $C_1$-$C_4$, alkoxy $C_1$-$C_4$, cyano and nitro; and W is selected from hydrogen, halogen, alkyl $C_1$-$C_4$, alkoxy $C_1$-$C_4$, cyano and nitro. The invention also relates to a method for the control of insects, comprising contacting the ova and/or the larvae of the insects with an ovicidally-larvicidally effective amount of a cyanomethyl thioester compound represented by formula (I) above and additionally, with formula (I) compounds, wherein R is also methyl or phenyl. The invention further relates to methods for the preparation of the formula (I) cyanomethyl thioesters and to insect ovicidal and larvicidal compositions comprising the cyanomethyl thioester(s) and an inert carrier therefor.

Preferred insect ovicidal-larvicidal compounds of this invention have the structure of formula (I), wherein X is oxygen or sulfur; R is $CH_3$—, $C_2H_5$—, $(CH_3)_3C$—,

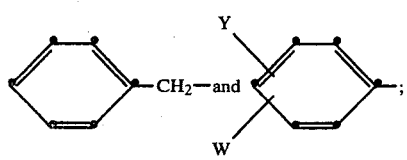

Y is $CH_3$—, $(CH_3)_3C$—$CH_3O$—, Cl, CN— and $NO_2$—; and W is hydrogen, $CH_3$—, $(CH_3)_3C$—, $CH_3O$—, Cl, NC— and $NO_2$—. Most preferred of these insect ovicides are compounds as described, where X is oxygen and R is $C_2H_5$—,

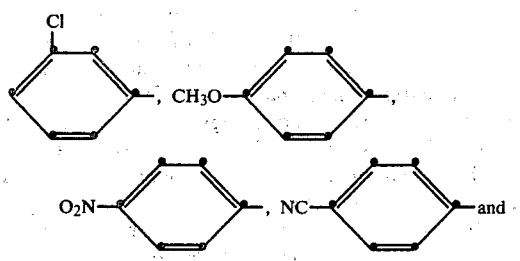

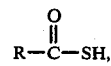

These latter compounds have the added advantage of low phytotoxicity to crops at rates of application employed in ovicidal applications. This reduced phytotoxicity is, of course, important in the treatment of crops, since excessive injury to crop plants will ultimately reduce crop yields and/or reduce the market value of the crop harvested, due to discoloration or marking of the fruit or foliage produced by the treated plants.

The compounds of this invention can be prepared by reacting a thioacid of formula:

$$R-\overset{O}{\underset{\|}{C}}-SH,$$

wherein R is alkyl $C_2$-$C_4$,

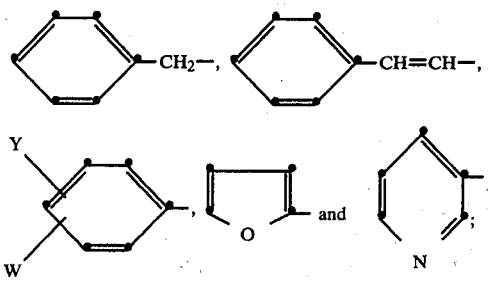

Y is halogen, alkyl $C_1$-$C_4$, alkoxy $C_1$-$C_4$, cyano and nitro; W is hydrogen, halogen, alkyl $C_1$-$C_4$, alkoxy $C_1$-$C_4$, cyano and nitro; with equimolar or excess amounts of chloroacetonitrile in the presence of a base such as triethylamine or other basic tertiary amines, sodium or potassium alkoxide of a $C_1$-$C_5$ alcohol, sodium or potassium carbonate, and the like, in an inert solvent such as ether, tetrahydrofuran (THF), dimethylformamide, and the like, at a temperature range of from about 0° C. to 30° C. for a period of time sufficient to essentially complete the reaction. The reaction mixture is then concentrated, taken up in ether, and the thus-formed solution washed with saturated sodium bicarbonate solution and saturated brine, and then dried, as for example, with sodium sulfate. The resulting solution is then concentrated to give the crude product. The crude product may be further purified by several means including crystallization, distillation, chromatography, or the like. The above reaction may be graphically illustrated as follows:

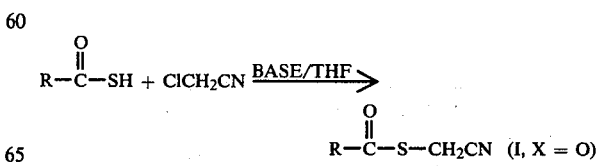

Alternatively, the compounds of this invention may be prepared by reacting an acid halide of formula

wherein R is as hereinabove defined, and Z is selected from chlorine or bromine, with equimolar or excess amounts of mercaptoacetonitrile in the presence of an acid acceptor such as an alkali metal carbonate selected from sodium or potassium carbonate, pyridine, or the like, in an inert solvent such as ether, tetrahydrofuran, benzene, toluene or xylene, and the like, at a temperature range of from about 10° C. to 30° C., for a period of time sufficient to essentially complete the reaction. The product of this reaction can be recovered and purified by work-up procedures similar to those described above. This reaction may be graphically illustrated as follows:

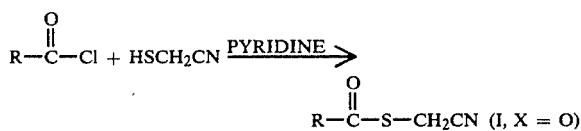

wherein R is as hereinabove defined.

A still further method for the preparation of the thioesters of the present invention represented by formula (I), wherein R is aryl or substituted aryl, involves the reaction of the corresponding aldehyde with sulfur and piperidine at elevated temperatures to yield the corresponding thioacylpiperidine, which is then reacted with chloro- or bromoacetonitrile to yield the corresponding pyridinium salt. Finally, this salt is reacted with water or hydrogen sulfide to afford a compound of formula (I), wherein X is oxygen or sulfur, respectively. This reaction sequence may be graphically illustrated as follows:

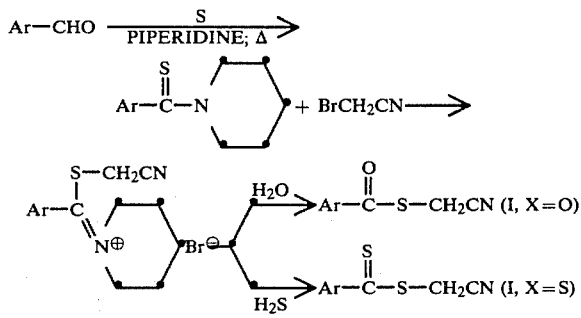

Still another method of interest for the preparation of the compounds of the present invention can be graphically illustrated and described as follows:

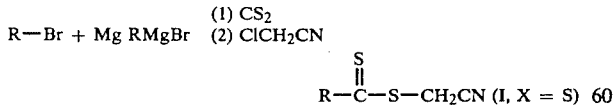

wherein in the above reaction sequence, R is as hereinabove defined. The Grignard reagent, RMgBr, is prepared from R-Br and Mg in an inert solvent such as tetrahydrofuran, at the boiling point of the solvent; the thus-formed solution of the Grignard reagent is chilled in a dry ice-acetone bath and carbon disulfide added. When the ensuing reaction is complete, the solution is filtered, and the intermediate contained therein is reacted with chloro- or bromoacetonitrile at room temperature. Finally, the reaction mixture is concentrated, the residue taken up in a suitable solvent, such as ether, the solution is washed with water, dried and then evaporated to afford the crude product. The product may be purified, if desired, by standard laboratory procedures such as recrystallization, distillation, chromatography, and the like.

Advantageously, the cyanomethyl thioesters represented by formula (I) above are highly effective ovicidal agents useful for inhibiting the hatching of eggs of insects and/or for preventing the development and maturation of the newly hatched larvae of the pests.

As insect ovicides, the formula (I) compounds are particularly effective for reducing the hatch of eggs of Lepidoptera, Coleoptera and Diptera.

Application of the above compounds for the control of insects is generally facilitated by employing a composition containing an ovicidally effective amount of the compound(s) in combination with an inert agricultural adjuvant. The compositions may be formulated as emulsifiable concentrates, dust, wettable powders, flowable (thixotropic) concentrates, and the like.

In practice, these compositions are generally dispersed in water or other inexpensive liquid diluent and applied as a spray to the foliage and stems of plants sought to be protected against attack from newly hatching larvae and to destroy the new generation of eggs oviposited by adult females on same.

Desired control of generally achieved with liquid compositions containing from about 1.0 ppm to about 1000 ppm of active ingredient applied at a rate of between about 10 and 50 liters per hectare using aerial application equipment or from about 50 to 1000 liters per hectare using ground application equipment. For mosquito control, the active ingredient may be dispersed in ponds, lakes, rivers, or the like, in an amount sufficient to provide at least about 0.04 ppm of the active ingredient.

A typical emulsifiable concentrate which may be used in the preparation of the above-identified compositions is as follows:

Emulsifiable Concentrate

50% by weight of S-cyanomethyl thiobenzoate,
38% by weight of cyclohexanone, and
12% by weight of a nonionic emulsifier.

A typical flowable concentrate may be prepared as follows:

Flowable Concentrate

45% by weight of S-cyanomethyl thiobenzoate,
50% by weight of water,
3% by weight of sugar-free, sodium-based sulfonates of Kraft lignin, and
2% by weight of Bentonite clay.

The ovicidal compositions of this invention are most effective for preventing the hatch of eggs of insects when brought into direct contact with the eggs; however, we have determined that certain of the formula (I) cyanomethyl thioesters advantageously also exhibit fumigant activity and this activity enhances the usefulness of these compounds. Such activity permits control of egg hatch and/or development of newly emerged larvae, by application of the active compound to the locus of the deposited eggs such that the toxicant vapors can come in contact with the eggs and/or emerging larvae.

The present invention is further illustrated by the examples set forth below.

EXAMPLE 1

Preparation of S-Cyanomethyl Thiobenzoate

Sodium methoxide (5.13 g; 0.095 mol) is added with stirring to an ice cold solution of thiobenzoic acid (13.8 g; 0.095 mol) in THF (100 ml). A yellow slurry forms. Next, chloroacetonitrile (6.45 ml; 0.10 mol) is added, and the reaction mixture stirred overnight at room temperature. It is then filtered, and the filtrate concentrated in vacuo to yield a yellow oil. This oil is dissolved in ether, the solution washed with saturated sodium bicarbonate solution, saturated salt solution, dried over sodium sulfate and concentrated in vacuo. The residual oil is distilled (boiling point 105°–106° C. at 10.5 mm) to afford 12.8 g (76%) of title product, a yellow oil.

Analysis calculated for $C_9H_7NOS$: C, 61.00; H, 3.98; N, 7.90. Found: C, 60.88; H, 4.14; N, 8.00.

Infrared and nuclear magnetic resonance spectra confirm the proposed structure.

By the above procedure, but substituting thioacetic acid and thiopropionic acid for thiobenzoic acid, S-cyanomethyl thioacetate and S-cyanomethyl thiopropionate, boiling point 65°–66° C./1.0 mm, are obtained, respectively.

EXAMPLE 2

Preparation of Cyanomethyl Dithiopropionate.

The magnesium bromide salt of dithiopropionic acid is prepared by the procedure of Meijer et al. [*Recueil* 92: 601 (1973)] as follows:

A mixture of magnesium (6.24 g; 0.26 mol) and THF (50 ml) is stirred and heated to reflux. Ethyl bromide (15.2 ml; 0.20 mol) is added to the above mixture at a rate to keep the THF refluxing. After the addition is completed, the Grignard reagent is cooled in a dry ice-acetone bath to about −10° C. and held at that temperature throughout the addition of carbon disulfide (13.2 mol; 0.22 mol). One hour after the addition is completed, the reaction mixture is warmed to room temperature and filtered.

The above prepared solution of the magnesium bromide salt of dithiopropionic acid is cooled to 10° C. and chloroacetonitrile (13 ml; 0.195 mol) added at a rate such that the temperature of the reaction mixture slowly rises to 25° C. After the addition is completed, the reaction mixture is stirred one hour at room temperature, and then concentrated in vacuo. The residue is dissolved in ether, the solution washed with saturated salt solution, dried over sodium sulfate and concentrated in vacuo to yield 18 g of a red oil. This oil is chromatographed on silica gel (300 g) and eluted with a 1:3 hexane:methylene chloride mixture to afford 12.1 g of title product, a red oil. Infrared and nuclear magnetic resonance spectra confirm the proposed structure.

An identical sample from another preparation is distilled (boiling point 72° C. at 0.5 mm) and chromatographed.

Analysis calculated for $C_5H_7NS_2$: C, 41.35; H, 4.86; N, 9.64. Found: C, 41.60; H, 4.93; N, 9.65.

By the above procedure, but substituting bromobenzene for ethyl bromide, cyanomethyl dithiobenzoate, melting point 43°–46° C., is prepared.

EXAMPLE 3

Preparation of 1-(p-Chlorothiobenzoyl)piperidine.

To a suspension of sulfur (9.6 g; 0.30 mol) in piperidine (30 ml; 0.30 mol) is added p-chlorobenzaldehyde 28.1 g; 0.20 mol) and the mixture heated at reflux for one hour. The hot reaction mixture is then poured into water and filtered. The solid is recrystallized from ethanol to afford 38.4 g of title product in two fractions. A 5.0 g sample is recrystallized from methylene chloride and hexane to yield 4.4 g of light yellow solid, melting point 105°–112° C. (lit. melting point 108°–109° C.). Infrared spectra confirms the proposed structure.

By the above procedure, but substituting p-methoxybenzaldehyde for p-chlorobenzaldehyde, 1-(p-methoxythiobenzoyl)piperidine is obtained.

EXAMPLE 4

Preparation of 1-[p-Chloro-α-(cyanomethylthio)benzylidene]-piperidinium Bromide.

Bromoacetonitrile (18.4 g; 0.153 mol) is added to a stirred suspension of 1-(p-chlorothiobenzoyl)piperidine (33.4 g; 0.139 mol) in toluene (100 ml). The reaction mixture becomes a clear solution within one hour, then a precpitate begins to form. The reaction mixture is then stirred overnight at room temperature, diluted with ether and filtered to yield a light yellow, hygroscopic, solid. This solid is dried in vacuo to afford 29.5 g of title product, melting point 114°–120° C. A 5.0 g sample is recrystallized from ethanol-ether to yield 3.1 g of a white solid, melting point 117°–125° C.

Analysis calculated for $C_{14}H_{16}BrClN_2 \cdot \frac{1}{2}H_2O$: C, 45.60; H, 4.65; N, 7.60. Found: C, 45.35; H, 4.87; N, 7.55.

By the above procedure, but substituting 1-(p-methoxythiobenzoyl)-piperidine for 1-(p-chlorothiobenzoyl)piperidine, 1-[p-methoxy-α-(cyanomethylthio)benzylidene]piperidinium bromide is obtained.

EXAMPLE 5

Preparation of S-Cyanomethyl p-Chlorothiobenzoate.

A suspension of 1-[p-chloro-α-(cyanomethylthio)benzylidine]piperidinium bromide (10.0 g; 0.278 mol) in water (100 ml) and ethanol (25 ml) is stirred at room temperature overnight. The slurry is then filtered to afford 4.4 g of pale yellow solid. This solid is dissolved in methylene chloride, and the solution filtered through 40 g of silica gel, isolated from the solution and recrystallized from a methylene chloride-hexane mixture to afford 3.5 g (59%) of a light tan solid, melting point 79°–81° C.

Analysis calculated for $C_9H_6ClNOS$: C, 51.07; H, 2.86; N, 6.62. Found: C, 50.85; H, 2.91; N, 6.53.

Infrared and nuclear magnetic resonance spectra confirm the proposed structure.

By the above procedure, but substituting 1-[p-methoxy-α-(cyanomethylthio)benzylidene]-piperidinium bromide for 1-[p-chloro-α-cyanomethylthio)benzylidene]piperidinium bromide, S-cyanomethyl p-methoxythiobenzoate, melting point 81°–84° C., is obtained.

EXAMPLE 6

Preparation of p-Chlorodithiobenzoic Acid Cyanomethyl Ester.

Hydrogen sulfide gas is added to a stirred suspension of 1-[p-chloro-α-(cyanomethylthio)benzylidene]-piperidinium bromide (13.7 g; 0.037 mol) in ethanol (50 ml), using a dry ice condenser to contain the gas. The reaction mixture slowly becomes a clear, red solution and the temperature rises to 25° C. The reaction mixture is chilled to −20° C., and an excess of hydrogen sulfide is maintained in the reaction mixture for 3 hours, as evidenced by the condensation of same throughout this period in the dry ice, chilled condenser. The reaction mixture is then allowed to warm up to room temperature, and the excess hydrogen sulfide allowed to evaporate overnight. The reaction mixture is then concentrated in vacuo to yield 8.9 g of a red oil. The red oil is chromatographed on silica gel (300 g) and eluted with a 1:1 mixture of methylene chloride:hexane. Collection of the main fraction affords 4.25 g (50%) of title product, a red oil.

Analysis calculated for $C_9H_6NS_2$: C, 47.47; H, 2.66; N, 6.15. Found: C, 47.74; H, 2.90; N, 6.24.

EXAMPLE 7

Preparation of Sodium Trithiocarbonate.

The title product is prepared by a method described by D. J. Martin et al. [*Journal Organic Chemistry* 33: 1275 (1968)] as follows:

A well-stirred mixture of sodium sulfide (103.0 g; 0.43 mol), water (50 ml) and carbon disulfide (36 ml) is heated at 40° C. overnight. The excess carbon disulfide is then removed in vacuo and the volume of the solution adjusted to 200 ml with water (2.15 M solution).

EXAMPLE 8

Preparation of Mercaptoacetonitrile.

Chloroacetonitrile (13.3 ml; 15.86 g; 0.203 mol) is added dropwise to a well-stirred mixture of aqueous sodium trithiocarbonate solution (100 ml, 0.215 mol) and ether (100 ml). The temperature of the reaction mixture is maintained below 15° C. The reaction mixture is stirred for one hour, the phases separated, and the ether phase discarded.

The aqueous phase is acidified to pH 4 with 6 N hydrochloric acid, while cooling in an ice bath and simultaneously extracting with ether (100 ml). The aqueous layer is extracted with another portion of ether, the ether layers are combined, washed with brine, dried over sodium sulfate and concentrated in vacuo to afford 12.0 g of product, a brown oil. This oil is diluted with ether to afford a 1.64 molar solution of title product, to be used in subsequent reactions without further purification.

Samples from other preparations were further purified by chromatography or by distillation, boiling point 18° C. at 0.2 mm; infrared and nuclear magnetic resonance spectra confirm the proposed structure.

EXAMPLE 9

Preparation of S-Cyanomethyl 2-Thiofuroate.

To an ice cold solution of furoyl chloride (4.0 ml; 0.04 mol) in ether (100 ml) is added dropwise a freshly prepared solution of pyridine (3.24 ml; 0.04 mol) in 1 N mercaptoacetonitrile (40 ml; 0.04 mol). After the addition is completed, the mixture is allowed to stir at room temperature overnight. The reaction mixture is then washed with water, saturated sodium bicarbonate solution, saturated brine, dried over sodium sulfate, and is concentrated in vacuo. The residue (6.0 g) is filtered through a 25 g column of silica gel and eluted with methylene chloride. The methylene chloride eluent is diluted with hexane, cooled and filtered to yield 4.3 g (64%) of title product, an orange solid, melting point 76°–78° C. Recrystallization from methylene chloride-hexane affords 3.7 g product, as a pale orange solid, melting point 77°–78° C.

Analysis calculated for $C_7H_5NO_2S$: C, 50.29; H, 3.01; N, 8.38. Found: C, 50.04; H, 3.13; N, 8.34.

Infrared and nuclear magnetic resonance spectra confirm the proposed structure.

EXAMPLE 10

By the procedures of Examples 7 to 9, the following compounds are prepared:

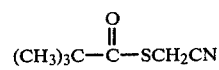

boiling point 120°–122° C./20 mm

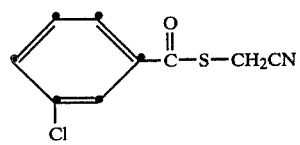

melting point 65°–66.5° C.

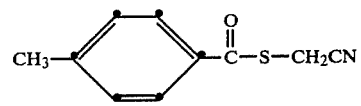

melting point 57°–58° C.

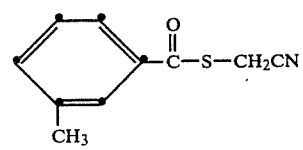

boiling point 112°–116° C./0.05 mm

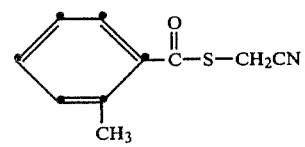

boiling point 109° C./0.05 mm

boiling point 120°–124° C./0.05 mm

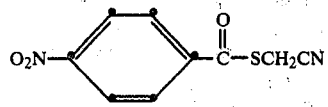

melting point 90°–92° C.

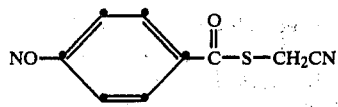

melting point 132°–134° C.

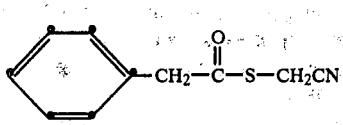

boiling point 115°–117° C./0.05 mm

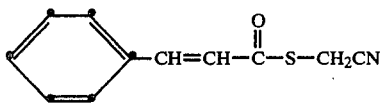

melting point 80°–83° C.

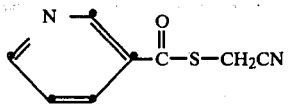

melting point 58°–60° C.

EXAMPLE 11

Preparation of p-Cyanothiobenzoic Acid S-Cyanomethyl Ester.

Chloroacetonitrile (13.1 ml; 0.203 mol) is added over 15 minutes to a cold (15° C.) 2 N solution of sodium trithiocarbonate (92.5 ml; 0.185 mol). The reaction mixture is stirred one hour at 5° C., extracted with ether, and the aqueous layer added dropwise to a solution of p-cyanobenzoyl chloride (20.9 g; 0.124 mol) in dichloromethane (40 ml). During addition, the temperature of the reaction mixture is held below 12° C. The reaction mixture is then held at 0°–5° C. for 2 hours, diluted with hexane (50 ml) and filtered to yield 26 g of a yellow solid. This solid is recrystallized from a mixture of acetone-methanol-water to afford 19.7 g of title product, a yellowish solid, melting point 129°–131° C.

An analytical sample is prepared by chromatograping 0.1 g of crude product in silica gel and eluting with a mixture of methylene chloride-hexane. The sample is then recrystallized from the eluent to yield the product, a white solid, melting point 132°–134° C.

Analysis calculated for $C_{10}H_6N_2OS$: C, 59.39; H, 2.99; N, 13.85. Found: C, 59.25; H, 3.35; N, 13.86.

EXAMPLE 12

Evaluation as Ovicidal Agents of Compounds having the Structure:

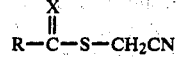

is Determined using the Procedures, Insects and Acarina Described Below.

Tobacco Budworm (*Heliothis virescens*) Egg Test.

A cotton plant with the first true leaf expanded to about 7 cm in length is dipped into a 50/50 acetone/water mixture containing 100, 10 or 1 ppm of test compound. A 10 to 20 mm square of cheesecloth containing 50–100 budworm eggs 6 to 30 hours old is also dipped in the test solution, placed on the treated leaf, and the combination placed in a hood to air dry. When dry, the leaf with eggcloth still attached is removed from the plant and placed in a 250 g cup to which a 5 cm length of damp cotton dental wick has been previously added. A clear plastic lid is placed on the cup and the cup held at 27° C. for 2 days. After 2 days, the leaf and cheesecloth are examined under a low power microscope to determine egg hatch. Data obtained are reported below as percent mortality of the eggs (Table I).

Malaria Mosquito (*Anopheles quadrimaculatus*) Eggs and 1st Instar Test

Test solutions are prepared as 50/50 acetone/water mixtures containing 0.4 or 0.04 ppm of test compound. A 250 ml test solution is placed in a 400 ml beaker, and a wax paper ring about one cm wide and 6.5 cm in diameter is floated on the surface of the test solution to keep the eggs from floating up the meniscus curve and drying out on the side of the beaker, and about 100 eggs (6 to 30 hours old) are then introduced into the test solution. After the beaker is held at 27° C. for 2 days, the contents are examined and the percent kill of eggs noted and recorded. Percent kill of newly hatched larvae and delayed hatch are, likewise, noted if such occur. Data obtained are reported in Table I.

Tobacco Budworm (*Heliothis virescens*), Closed Chamber Fumigation Test.

A 15 mg sample of test compound is dissolved in 10 ml of acetone. One ml of this is then pipetted evenly over the bottom of a 150 mm diameter petri dish which is then set aside to allow the acetone to evaporate. This is the equivalent of 1.12 kg/ha applied on a broadcast basis to the dish. Lower rates may be prepared by appropriate dilutions of the initial test solution. The petri dish is then placed in a 4-liter battery jar covered with a glass lid. The lid has been previously prepared such that a square of cheesecloth with 50 to 100 budworm eggs has been hung on a clip fastened to the underside of the lid with a piece of tape. The eggs are thus suspended 6 to 8 cm below the lid and centered over the petri dish. The battery jar is then held for 3 days at 27° C. After 3 days, the eggcloths are examined under a 10X microscope, and the eggs counted as dead, hatched or infertile. Percent kill is calculated from: (number dead/number dead+number hatched)×100. Data obtained are reported as percent kill (Table 1).

Cotton Bud Phytotoxicity Test.

In this test, 50/50 acetone/water mixtures containing 1000 ppm of 500 ppm of test compound are prepared. Young cotton plants with leaf buds showing are dipped in the test solution and placed in a hood to dry, then held at 27° C. for 2 weeks to determine whether the cotton buds have been injured by the treatment. Injury is rated on a scale of 0 to 5; 0 being no injury and 5 being complete kill.

Data from the above test are reported in Table 1 below.

Tobacco Budworm (*Heliothis virescens*), Egg, Open Cage Oviposition Test.

About 75–100 budworm pupae of mixed sexes are put in a screen cage neasuring 30×30×30 on a day before they are due to emerge as moths. Several cotton plants are maintained in the cage and examined daily for eggs. When eggs are seen, the plants are removed, and the test is ready to begin, usually 3–5 days after emergence.

Cotton plants with two fully-expanded leaves are selected and dipped in the appropriate concentrations in 50:50 acetone:water and placed in the hood to dry. Excessive drying time is to be avoided. As soon as the plants are dry, they are placed in the cage with the moths. Plants are randomly assigned to cages, 4 plants to a cage. The plants are removed daily and replaced by freshly treated plants.

Holding Conditions

The cages are placed in an incubator maintained at 30° C. for a 16-hour day and at 25° C. for an 8-hour night. Upon removal from the cages, the plants are maintained at 27° C. until the eggs hatch, usually in about 3 days.

Observations

Upon emergence of the larvae, the leaves and terminals are examined under a 10X microscope and counts made of dead, hatched and infertile eggs, as well as dead and alive larvae.

Infertile eggs are not counted when calculating the percent kill.

TABLE I

Evaluation of the Ovicidal Activity of the Compounds of the Invention $$R-\overset{\overset{X}{\|}}{C}-S-CH_2CN$$

| R | X | % Kill Mosquito Eggs 0.4 ppm | % Kill Mosquito Eggs 0.04 ppm | % Kill Mosquito Eggs 0.004 ppm | % Kill Tobacco Budworm Eggs 100 ppm | % Kill Tobacco Budworm Eggs 10 ppm | % Kill Tobacco Budworm Eggs 1 ppm | % Kill - Tobacco Budworm Eggs Closed Jar Fumigation Test 1.12 kg/ha | % Kill - Tobacco Budworm Eggs Closed Jar Fumigation Test 0.112 kg/ha | Cotton Bud Phytotoxicity 1000 ppm* | Cotton Bud Phytotoxicity 500 ppm* | Cotton Bud Phytotoxicity 250 ppm* | % Kill - Tobacco Budworm Eggs Open Cage Test 1000 ppm | % Kill - Tobacco Budworm Eggs Open Cage Test 300 ppm |
|---|---|---|---|---|---|---|---|---|---|---|---|---|---|---|
| CH₃— | 0 | 0 | | | 100 | 0 | | 99 | 0 | 1 | | | 0 | |
| C₂H₅— | 0 | 100 | 0 | | 100 | 0 | | <10 | | 2.5 | 0 | | <10 | |
| C₂H₅— | S | 100 | 0 | | 100 | 0 | | — | — | — | | | — | |
| (CH₃)₃C— | 0 | 0 | | | 0 | | | — | | 4 | | | 0 | |
| ⌬ (phenyl) | 0 | 86–99 | 0 | | 100 | 100 | 86–99 | 94 | 12 | 5 | 4.5 | 0 | 50, 0 / 23, 0 | 27 / 0 / 0 |
| ⌬ (phenyl) | S | 100 | 0 | | 100 | 71–85 | 0 | 0 | | 5 | 2 | 1 | 0 | |
| Cl—⌬ | 0 | 100 | 41–60 | 0 | 100 | 100 | 71–85 | 0 | | 5 | | | <10 | |
| Cl—⌬ | S | 100 | 41–60 | 0 | 100 | 100 | 0 | 15 | | 5 | | | 0 | |
| Cl—⌬ | 0 | 100 | 41–60 | | 100 | 100 | 0 | 3 97+ | 0 | 2 | | | 0 | |
| CH₃—⌬ | 0 | 100 | 0 | | 100 | 100 | 0 | 24 76+ | 0 50+ | 5 | | | 0 | |
| CH₃—⌬ | 0 | 100 | 0 | | 100 | 86–99 | 5 | 0 | | 4 | | | 0 | |
| CH₃-⌬ | 0 | 100 | 0 | | 100 | 86–99 | 0 | 50 50+ [88; 12+] | 0 | 4 | | | 0 | |
| (CH₃)₃C—⌬ | 0 | 0 | | | 100 | 100 | 0 | 0 | | 5 | | | <10 | |
| CH₃O—⌬ | 0 | 100 | 0 | | 100 | 86–99 | 0 | <10 | | 2 | | | 0 | |

TABLE I-continued
Evaluation of the Ovicidal Activity of the Compounds of the Invention $$R-\overset{X}{\underset{\|}{C}}-S-CH_2CN$$

| R | X | % Kill Mosquito Eggs 0.4 ppm | % Kill Mosquito Eggs 0.04 ppm | % Kill Mosquito Eggs 0.004 ppm | % Kill Tobacco Budworm Eggs 100 ppm | % Kill Tobacco Budworm Eggs 10 ppm | % Kill Tobacco Budworm Eggs 1 ppm | % Kill - Tobacco Budworm Eggs Closed Jar Fumigation Test 1.12 kg/ha | % Kill - Tobacco Budworm Eggs Closed Jar Fumigation Test 0.112 kg/ha | Cotton Bud Phytotoxicity 1000 ppm* | Cotton Bud Phytotoxicity 500 ppm* | Cotton Bud Phytotoxicity 250 ppm* | % Kill - Tobacco Budworm Eggs Open Cage Test 1000 ppm | % Kill - Tobacco Budworm Eggs Open Cage Test 300 ppm |
|---|---|---|---|---|---|---|---|---|---|---|---|---|---|---|
| O₂N—⌬— | 0 | 86–99 | 0 | | 100 | 0 | | 0 | | 0 | | | 0 | |
| NC—⌬— | 0 | 0 | | | 100 | 41–60 | | 0 | | 0 | | | 20 | 80+ |
| ⌬—CH₂— | 0 | 86–99 | 0 | | 100 | 71–85 | | 0 | 100+ | 0 | | 5 | | |
| ⌬—CH=CH— | 0 | 100 | 0 | | 100 | 100 | 0 | 0 | | | | 3.5 | <10 | |
| furyl | 0 | 0 | | | 100 | 0 | | 100 | 0 | | | 5 | 0 | |
| pyridyl | 0 | 0 | | | 100 | 0 | | 0 | | | 4 | | 0 | |

*Scale: 0 to 5 (0 = No Injury, 5 = Killed
+: Percent kill of newly hatched larvae

We claim:
1. A compound of the formula

$$R-\overset{O}{\underset{\|}{C}}-S-CH_2CN$$

wherein R is C₂H₅—, (CH₃)₃C—,

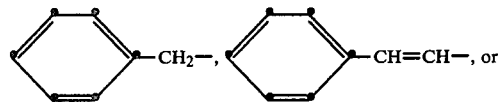

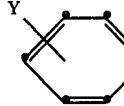

Y is Cl, CH₃—, (CH₃)₃C—, CH₃O—, cyano or nitro.

2. A compound of the formula $$R-\overset{S}{\underset{\|}{C}}-S-CH_2CN$$

wherein R is C₂H₅— or

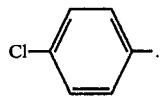

3. A compound thiopropionic acid, S-cyanomethyl ester.
4. A compound 2,2-dimethylthiopropionic acid, S-cyanomethyl ester.
5. A compound p-chlorothiobenzoic acid, S-cyanomethyl ester.
6. A compound p-chlorodithiobenzoic acid, cyanomethyl ester.
7. A compound m-chlorothiobenzoic acid, S-cyanomethyl ester.
8. A compound p-thiotoluic acid, S-cyanomethyl ester.
9. A compound m-thiotoluic acid, S-cyanomethyl ester.
10. A compound p-thioanisic acid, S-cyanomethyl ester.
11. A compound p-nitrothiobenzoic acid, S-cyanomethyl ester.
12. A compound p-cyanothiobenzoic acid, S-cyanomethyl ester.
13. A compound phenylthioacetic acid, S-cyanomethyl ester.
14. A method for the control of insects, comprising contacting the ova and newly hatched larvae of the insects with an ovicidally-larvicidally effective amount of a compound of the formula:

$$R-\overset{X}{\underset{\|}{C}}-S-CH_2CN$$

wherein X is oxygen or sulfur; R is alkyl C₁–C₄, phenyl,

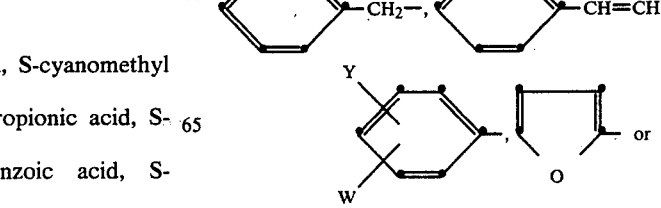

-continued

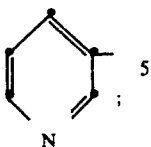

Y is halogen, alkyl $C_1$-$C_4$, alkoxy $C_1$-$C_4$, cyano or nitro; and W is hydrogen, halogen, alkyl $C_1$-$C_4$, alkoxy $C_1$-$C_4$, cyano or nitro.

15. A method according to claim 14, wherein X is oxygen; R is $CH_3$—, $C_2H_5$—, $(CH_3)_3C$—,

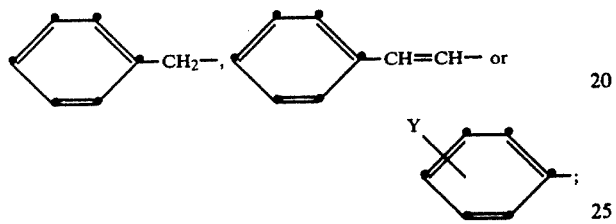

and Y is hydrogen, Cl, $CH_3$—, $(CH_3)_3C$—, $CH_3O$—, cyano or nitro.

16. A method according to claim 14, wherein X is sulfur; and R is $C_2H_5$—,

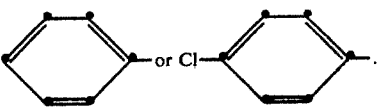

17. A method according to claim 14, wherein the compound is applied to the locus, wherein the insect eggs are deposited, in the form of a liquid spray containing from about 1.0 ppm to about 1000 ppm of the cyanomethyl thioester compound and at a rate from 10 to 1000 liters of said liquid per hectare.

18. A method according to claim 14, wherein the compound is thiopropionic acid, S-cyanomethyl ester.

19. A method according to claim 14, wherein the compound is p-thioanisic acid, S-cyanomethyl ester.

20. A method according to claim 14, wherein the compound is p-nitrothiobenzoic acid, S-cyanomethyl ester.

21. A method according to claim 14, wherein the compound is p-cyanothiobenzoic acid, S-cyanomethyl ester.

22. A method according to claim 14, wherein the compound is phenylthioacetic acid, S-cyanomethyl ester.

* * * * *